United States Patent [19]

Ikushima et al.

[11] Patent Number: 4,530,845

[45] Date of Patent: Jul. 23, 1985

[54] 1,4-NAPTHOQUINONE DERIVATIVES AND USE THEREOF

[75] Inventors: Koichi Ikushima, Toyonaka; Hirokazu Tanaka, Takarazuka; Ohe Osamu, Osaka; Eiko Kino, Hadano; Masanobu Kohsaka, Sakai; Hatsuo Aoki, Ikeda; Akira Arakawa, Kusatsu; Hiroshi Imanaka, Osaka, all of Japan

[73] Assignee: Fujisawa Pharmaceutical Co., Ltd., Osaka, Japan

[21] Appl. No.: 511,268

[22] Filed: Jul. 6, 1983

Related U.S. Application Data

[62] Division of Ser. No. 317,897, Oct. 31, 1981, Pat. No. 4,414,226.

[30] Foreign Application Priority Data

Mar. 6, 1980 [JP] Japan .................................. 55-29675

[51] Int. Cl.³ ..................... A61K 31/19; A61K 31/12; C07C 50/12
[52] U.S. Cl. ............................... 514/453; 260/396 R; 514/548; 514/569
[58] Field of Search ................... 260/396 R; 424/331, 424/317, 279

[56] References Cited

U.S. PATENT DOCUMENTS

| | | | |
|---|---|---|---|
| 2,301,382 | 11/1942 | Dickey et al. ..................... | 260/396 |
| 2,311,032 | 2/1943 | Dickey et al. ..................... | 260/396 |
| 3,578,686 | 5/1971 | Tullar et al. ...................... | 260/396 |
| 3,953,874 | 4/1976 | Aviram et al. .................... | 260/396 |

Primary Examiner—Richard L. Raymond
Assistant Examiner—Raymond Covington
Attorney, Agent, or Firm—Jordan B. Bierman

[57] ABSTRACT

1,4-naphthoquinone derivatives represented by the following general formula:

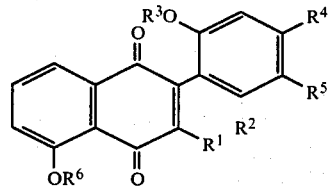

(wherein $R^1$ represents a hydrogen atom, a hydroxy group, a lower alkoxy group or an arylthio group, $R^2$ represents a carboxy group, an esterified carboxy group or an amidated carboxy group or, when taken together, $R^1$ and $R^2$ form a group of

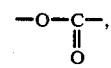

$R^3$ represents a hydrogen atom or a lower alkyl group, $R^4$ represents a lower alkyl group, $R^5$ represents a hydrogen atom or a halogen atom, and $R^6$ represents a hydrogen atom, a lower alkyl group or a lower alkanoyl group), and the salts of the carboxy group thereof, which are novel compounds having an anticoccidium activity, and which can be obtained by synthesis or, partly, by cultivation of Streptomyces auranticolor.

10 Claims, No Drawings

1,4-NAPTHOQUINONE DERIVATIVES AND USE THEREOF

This application is a divisional application of Ser. No. 317,897, filed on Oct. 31, 1981, now U.S. Pat. No. 4,414,226 and claims priority of Japanese application No. 29675/1980, filed on Mar. 6, 1980 pursuant to the Patent Cooperation Treaty, PCT No. JP81/00046.

This invention relates to new 1,4-naphthoquinone derivatives. More particularly, this invention relates to a new 1,4-naphthoquinone derivative, a salt of the carboxy group thereof, a method of production thereof, and an agent or composition containing said derivative or salt for the prophylaxis and treatment of coccidiosis.

The 1,4-naphthoquinone derivative as the subject matter compound of this invention is represented by the following general formula (I).

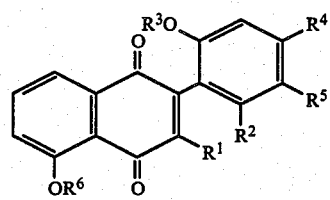

(wherein $R^1$ is hydrogen, hydroxy, lower alkoxy or arylthio; $R^2$ is carboxy, esterified carboxy or amidated carboxy; $R^1$ and $R^2$, taken together, may represent a group of

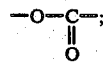

$R^3$ is hydrogen or lower alkyl; $R^4$ is lower alkyl; $R^5$ is hydrogen or halogen; $R^6$ is hydrogen, lower alkyl or lower alkanoyl).

The groups defined above will be explained below in detail. It should be understood that unless otherwise specificed, the term "lower" as used herein signifies a group containing 1 to 6 carbon atoms.

(1) $R^1$=lower alkoxy:

Examples of this lower alkoxy group include methoxy, ethoxy, propoxy, isopropoxy, butoxy, isobutoxy, sec-butoxy and tert-butoxy. Preferred is methoxy.

(2) $R^1$=arylthio:

This arylthio group is a substituted or unsubstituted arylthio group, which may for example be phenylthio, tolylthio, xylylthio, mesylthio or cumenylthio.

(3) $R^2$=esterified carboxy:

This esterified carboxy group may for example be a carboxy group esterified by a lower alkanol, such as lower alkoxycarbonyl (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.). Preferred is methoxycarbonyl.

(4) $R^2$=amidated carboxy:

This amidated carboxy group includes the amide formed between carboxy or a reactive derivative thereof and an unsubstituted or substituted amino compound. The amino compound includes not only urea, N,N-di-substituted derivatives thereof, substituted or unsubstituted aniline, and substituted alkylamino compounds of the general formula (II-1):

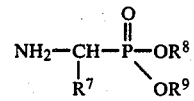

(wherein $R^7$, $R^8$ and $R^9$ each is hydrogen or lower alkyl), but also imide compounds. A typical imide compound is N,N'-dicyclohexylcarbodiimide. The reactive derivatives of carboxy include acid halides, acid anhydrides, active amides, active esters, etc.)

Preferred examples of the amidated carboxy group formed between carboxy and such an amino compound are carbamoyl, N-cycloalkyl-N-(N'-cycloalkylcarbamoyl)carbamoyl, N-(1-phosphonoethyl)carbamoyl, N-(1-O,O-di(lower)alkylphosphonoethyl)carbamoyl, N-phenylcarbamoyl, N-tolylcarbamoyl, N-(lower alkoxycarbonyl)phenylcarbamoyl, etc.

(5) $R^3$, $R^4$, $R^6$, $R^7$, $R^8$, $R^9$=lower alkyl:

Examples of this lower alkyl group are methyl, ethyl, propyl, isopropyl, butyl, isobutyl, tert-butyl, sec-butyl, etc., with methyl and ethyl being especially desirable.

(6) $R^6$=lower alkanoyl:

Examples of this lower alkanoyl group include acetyl, propionyl, butyryl, isobutyryl, valeryl, etc., with acetyl being particularly desirable.

(7) $R^5$=halogen:

This halogen atom may be fluorine, chlorine, bromine or iodine, with chlorine being especially desirable.

As regards the salts of carboxy function of the final compound (I) of this invention, there may be mentioned salts with inorganic or organic cations (e.g. sodium, potassium, calcium, aluminum, ammonium magnesium, triethylamine, ethanolamine, dicyclohexylamine, ethylenediamine, N,N'-dibenzylethylenediamine), salts with amino acids (e.g. arginine, aspartic acid, glutamic acid), etc.

The said compound (I) and said salt of carboxy function thereof can be produced in the following manner.

(I) Methods of Synthesis (1) Synthesis of compounds (I)

(i) Process A and Process B [Synthesis of Compounds (I-A), (I-B) and (I-C)]

Among the compounds (I), compounds of the undermentioned formulas (I-A), (I-B) and (I-C) can be produced by the routes illustrated below.

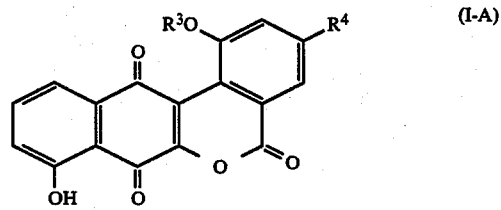

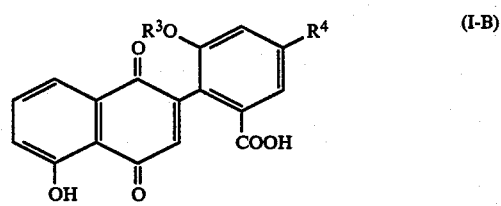

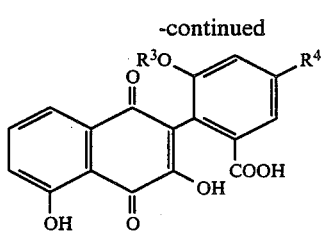
(I-C)

(wherein R³ and R⁴ are as defined hereinbefore)

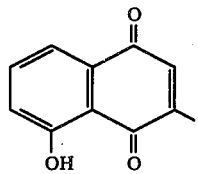
(II-2)

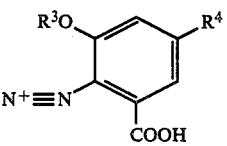
(II-3)

Process A ↓

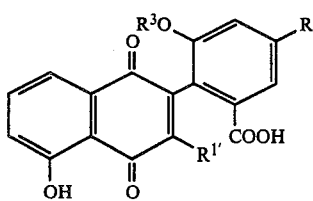
(I-B) or (I-C)

Process B ↓ (R¹' is hydroxy)

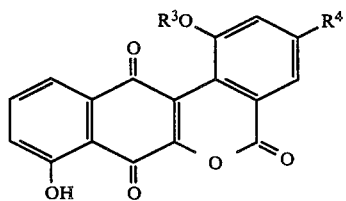
(I-A)

(wherein R¹' is hydrogen or hydroxy; R³ and R⁴ are as respectively defined hereinbefore)

Process A

In this process, a 1,4-naphthoquinone compound (II-2) is reacted with a diazo compound (II-3).

The compound (II-2) is a known compound while the compound (II-3) is a new compound and can be prepared by the method described hereinafter.

The reaction in this process is conducted in the conventional manner, usually in aqueous solution at room temperature or under warming.

Process B

In this process, the compound (I-C) [R¹' is hydroxy], which is among the reaction products obtainable by Process A, is reacted with a dehydrating agent in the per se conventional manner.

The dehydrating agent for this reaction may be one of those used commonly for esterification reactions. Preferred species are anhydrides of organic acids such as acetic anhydride, trifluoroacetic anhydride, etc. and carbodiimide compounds such as N,N'-dicyclohexyl-carbodiimide, etc.

This reaction is generally conducted in aqueous solution at room temperature or under warming.

(ii) Process C and Process D [conversion of compound (I-B) to compound (I-A)]

Among compounds (I), the compound (I-A) can also be produced from compound (I-B) in the following manner.

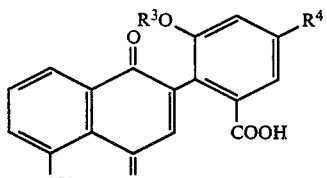
(I-B)

Process C ↓

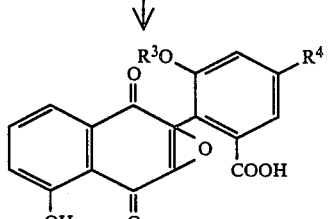
(I-B')

Process D ↓

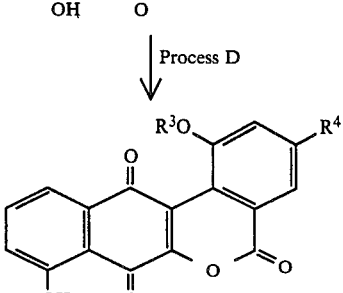
(I-A)

Process C

In this process, the compound (I-B) is reacted with as oxidizing agent, e.g. hydrogen peroxide, which is commonly utilized in the epoxidation of a double bond.

Generally this reaction is carried out in a solvent such as an alcohol (e.g. methanol, ethanol, etc.), dioxane or the like under cooling, at room temperature or under warming.

Process D

In this process, the compound (I-B') obtained in Process D is stirred under cooling in the presence of a catalyst such as hydrogen trifluoride and generally in a solvent such as methylene chloride, whereby (I-B') is converted to (I-A).

(iii) Process E and Process F [Synthesis of (I-C-1) and (I-C-1')]

Among compounds (I), the compound (I-C-1) and compound (I-C-1') can be produced in the following manner.

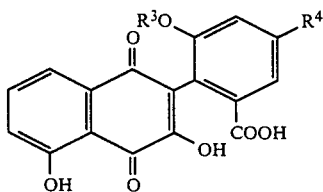
(I-C)

Process E ↓

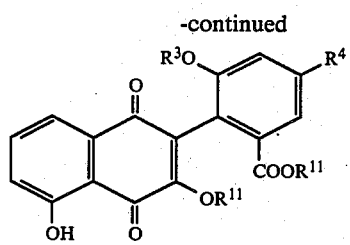

(I-C-1)

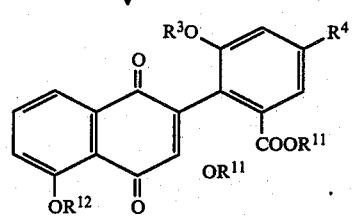

(I-C-1')

($R^3$ and $R^4$ are as respectively defined hereinbefore; $R^{11}$ and $R^{12}$ each is lower alkyl; X' is halogen or an acid residue such as an alkyl sulfate residue.)

Process E

The compound (I-C-1) can be produced by reacting compound (I-C) with a diazoalkane such as diazomethane or diazoethane.

This reaction is generally conducted in a solvent such as methanol or ethanol at room temperature.

Process F

The compound (I-C-1') can be produced by reacting compound (I-C-1), prepared in (iii)-i) above, with an alkylating agent (II-8). This reaction is generally conducted in the presence of silver oxide in a solvent such as chloroform at room temperature.

(iv) Process G and Process H [Synthesis of (I-C-2) and (I-A-1)]

Among compounds (I), compound (I-C-2) and compound (I-A-1) can be produced by the procedures depicted below.

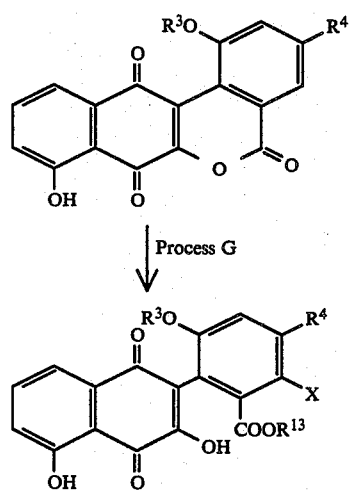

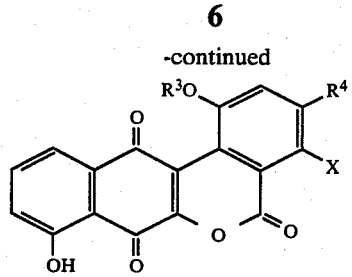

(I-A-1)

($R^{13}$ is lower alkyl; $R^3$, $R^4$ and X are as respectively defined hereinbefore.)

Process G

In this process, the compound (I-A) is treated with a halogenating agent in the presence of an alcohol $R^{13}$—OH.

The halogenating agent mentioned just above may for example be sulfuryl chloride or sulfuryl bromide.

This reaction is generally conducted in a solvent such as methylene chloride or acetic acid, but said alcohol $R^{13}$—OH may for example be methanol, ethanol or propanol may be relied on also as the solvent. It is also possible to use such solvents as a mixture. This reaction is generally carried out at room temperature or under warming.

Process H

The dehydrating agent which is used in this process may for example be an organic acid anhydride, e.g. acetic anhydride or trifluoroacetic anhydride, or one of the common dehydrating agents such as N,N'-dicyclohexylcarbodiimide.

This reaction is conducted at room temperature to under warming in a solvent similar to that mentioned for Process G.

(v) Process J [Synthesis of (I-A-3)]

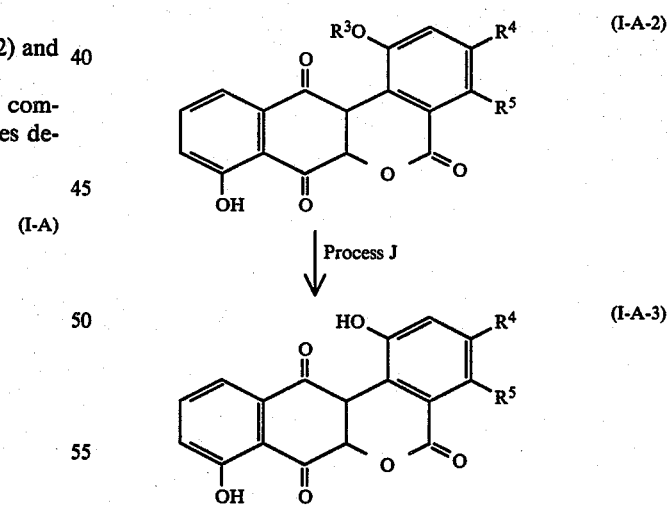

($R^3$, $R^4$ and $R^5$ are as respectively defined hereinbefore.)

Among compounds (I), compound (I-A-3) can be produced by reacting compound (I-A-2) with a boron trihalide.

Among compounds (I-A-2), the compound wherein $R^5$ is hydrogen is the above-mentioned compound (I-A) and the compound wherein $R^5$ is a halogen atom is the compound (I-A-1) mentioned in (iv) hereabove.

The boron trihalide may for example be boron trifluoride, boron tribromide or boron trichloride.

This reaction is generally conducted in a solvent such as methylene chloride under cooling or at room temperature.

(vi) Process K [Synthesis of (I-C-4)]

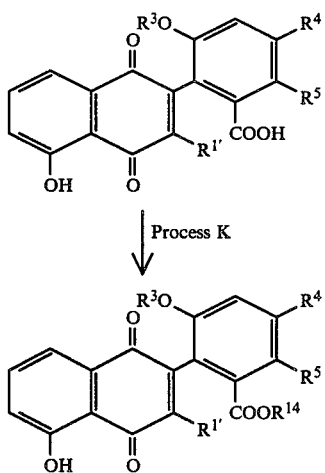

Process K

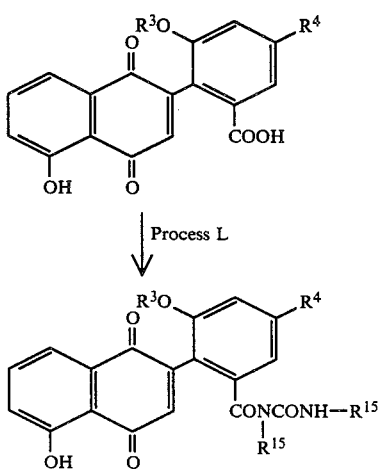

($R^{14}$ is lower alkyl; $R^{1'}$, $R^3$ and $R^4$ are as respectively defined hereinbefore.)

Among compounds (I), the compound (I-C-4) can be produced by esterifying compound (I-C-3).

The esterifying agent for this reaction may for example be a diazoalkane, some preferred species of which are diazomethane and diazoethane.

This reaction is generally conducted in a solvent such as an alcohol (e.g. methanol, ethanol) or diethyl ether or in a mixture of such solvents.

(vii) Process L [(Synthesis of (I-B-1)]

($R^3$ and $R^4$ are as respectively defined hereinbefore.)

Among compounds (I), the compound (I-B-1) can be produced by reacting compound (I-B) with a N,N'-dicycloalkylcarbodiimide $R^{15}$—N=C—N—$R^{15}$ ($R^{15}$ is cycloalkyl).

Preferred examples of said N,N'-dicycloalkylcarbodiimide are N,N'-dicyclopentylcarbodiimide and N,N'-dicyclohexylcarbodiimide.

The reaction is generally conducted in a solvent such as methyl chloride at room temperature.

(viii) Process M [Synthesis of (I-B-2)]

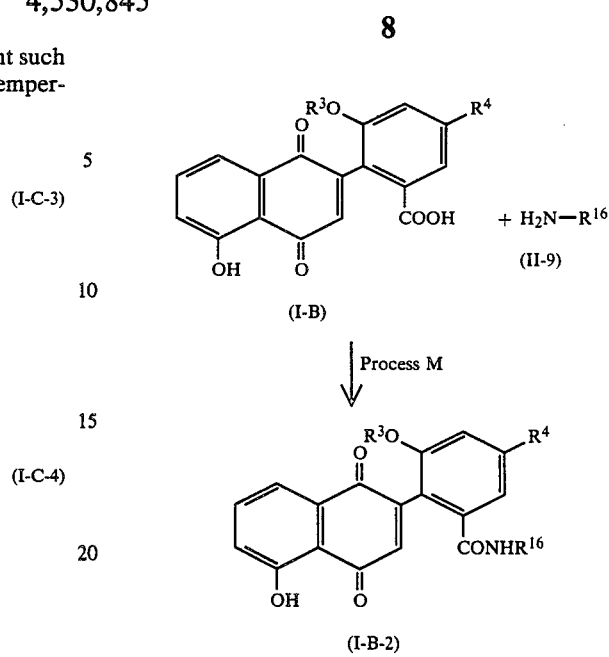

Process M

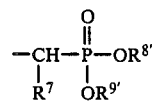

[$R^3$ and $R^4$ are as respectively defined hereinbefore; $R^{16}$ is hydrogen, substituted or unsubstituted phenyl or a group of formula:

$$-\underset{R^7}{\underset{|}{CH}}-\underset{OR^{9'}}{\underset{|}{\overset{O}{\overset{\|}{P}}}}-OR^{8'}$$

($R^7$ is as defined hereinbefore; $R^{8'}$ and $R^{9'}$ each is lower alkyl.)]

Among compounds (I), the compound (I-B-2) can be produced by reacting (I-B) or a reactive derivative of its carboxy function with (II-9).

When the above-mentioned compound (II-9) is such that $R^{16}$ is a substituted phenyl group, the substituent may for example be an esterified carboxy group such as lower alkoxycarbonyl. The reactive derivative of the carboxy function of compound (I-B) may for example be an acid halide (e.g. acid chloride). When the free carboxylic acid of (I-B) is used in this process, a condensing agent which is commonly used for amidation reactions is preferably employed. An example of such condensing agent is N,N'-dicyclohexylcarbodiimide.

This reaction is generally conducted in a solvent such as methylene chloride.

(xi) Process N [Synthesis of (I-B-3)]

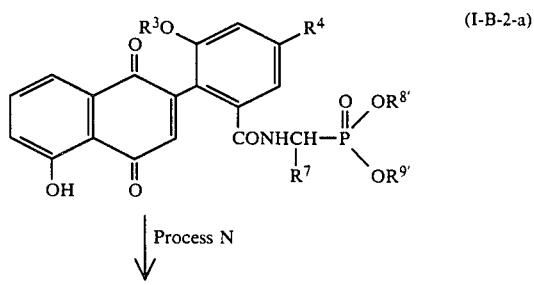

Process N

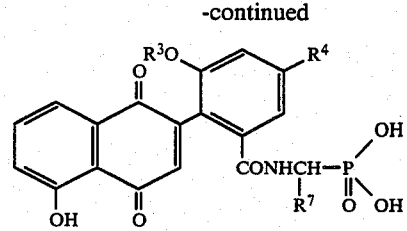
(I-B-3)

($R^3$, $R^4$, $R^7$, $R^{8'}$ and $R^{9'}$ are as respectively defined hereinbefore.)

Among compounds (I), the compound (I-B-3) can be produced by reacting the compound (I-B-2) wherein $R^{16}$ is

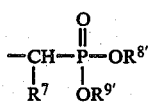

(I-B-2-a), which is obtainable in (viii), with a tri-lower alkyl silyl halide such as trimethyl silyl halide and, then, hydrolyzing the reaction product with water.

This reaction is generally conducted in aqueous solution at room temperature.

(x) Process O [Synthesis of (I-B-4)]

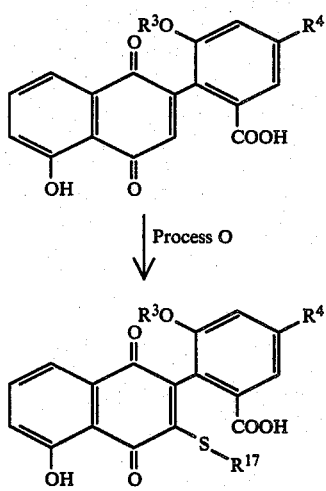

($R^3$ and $R^4$ are as respectively defined hereinbefore; $R^{17}$ is substituted or unsubstituted aryl.)

Among compounds (I), the compound (I-B-4) can be produced by reacting said compound (I-B) with an arylthiol compound HS—$R^{17}$ (II-10).

When $R^{16}$ in the formula (II-10) is substituted aryl, the substituent may for example be lower alkyl.

This reaction is generally conducted in a solvent such as methanol or ethanol at room temperature.

(xi) Process P [Synthesis of (I-C-5)]

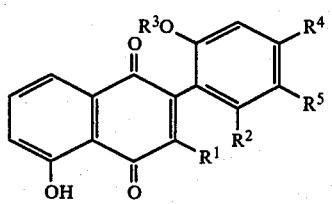
(I')

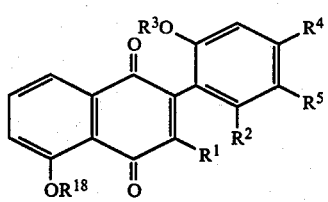
(I-C-5)

($R^1$, $R^2$, $R^3$, $R^4$ and $R^5$ are as respectively defined hereinbefore; $R^{18}$ is lower alkanoyl.)

The compound (I-C-5) can be produced by reacting a compound (I) wherein RHu 6 is hydrogen, which is a compound of formula (I'), with an acylating agent.

The acylating agent just mentioned above may be a lower alkanoic acid or a reactive derivative thereof, the latter being exemplified by acid halides (e.g. acid chloride, acid bromide) and acid anhydrides.

Generally, this reaction is preferably conducted in the presence of an inorganic or organic base, of the type commonly used, in a solvent at room temperature.

(2) Synthesis of starting compounds (i) Synthesis of compound (II-3)

The compound (II-3) for Process A can be produced by diazotizing the compound (II-3'):

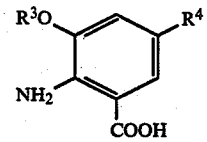
(II-3')

($R^3$ and $R^4$ are as respectively defined hereinbefore) in the per se conventional manner.

This compound (II-3') is a new compound which can be produced by the following route of synthesis.

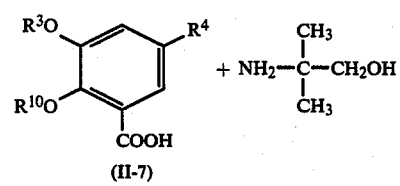
(II-7)

-continued

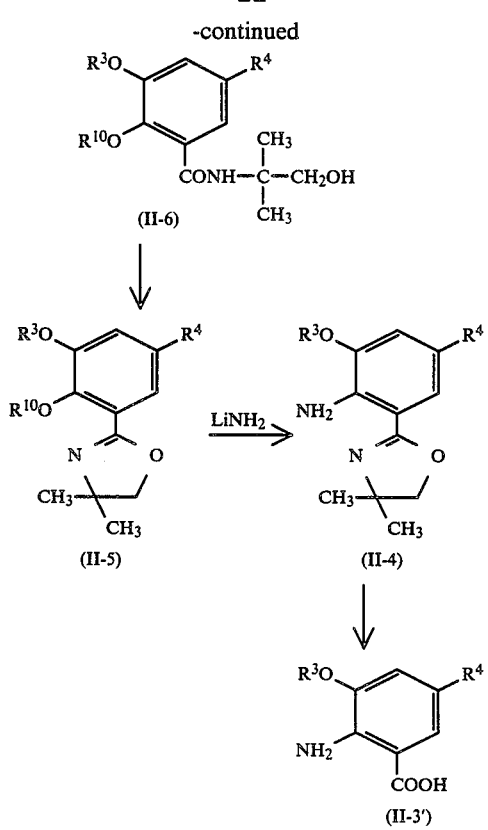

($R^3$ and $R^4$ are respectively defined hereinbefore; $R^{10}$ is lower alkyl.)

Thus, compound (II-7) and 2-amino-2-methyl-propanol are subjected to amidation reaction in the conventional manner to give (II-6) which is then reacted with a dehydrating agent to give (II-5). This compound (II-5) is further reacted with lithiumamide, preferably in a stream of nitrogen gas, to give the compound (II-4) which is then hydrolyzed to (II-3').

Among the compounds (I) and the salts of carboxy functions thereof, the compound having the following formula (Ia) can also be produced by fermentation.

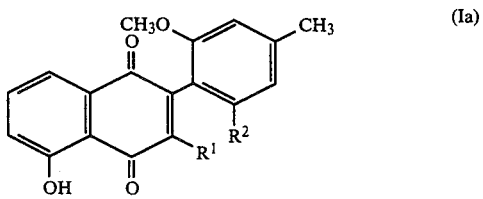

($R^1$ and $R^2$ taken together represent

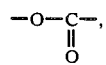

$R^1$ is hydrogen and $R^2$ is carboxy, or $R^1$ is hydroxy and $R^2$ is carboxy).

The fermentation process will be described in detail below.

The compound (Ia) can be produced by cultivating a (Ia)-producing strain of the genus Streptomyces, such as *Streptomyces auranticolor*, in the per se conventional manner.

As one of the (Ia)-producing strains of the genus Streptomyces, the strain herein designated as No. 5995, which the present inventors isolated from a soil sample collected in the mountain of Takao-San in Tokyo Prefecture, has the following bacteriological characteristics.

(i) Morphology:

The strain was incubated on sucrose-nitrate agar, glycerin-asparagine agar, yeast maltose-agar, oatmeal agar, and starch-inorganic salt agar at 30° C. for 10 to 14 days and its morphological characters on these media were microscopically examined.

Branching of sporulated hyphae: monopodial
Morphology of sporulated hyphae: spiral
The aerial mycelium is branched, terminating in open spirals.
Surface of spores: smooth
Size of spores: 0.5–1.1μ×0.9–1.7μ
Number of spores: 10–50
Position of sporophore: on aerial mycelium
Flagellum: not observed
Sporangium: not observed
Scelotium: not observed
Vegetative mycelium: not fragmented (ii) Cultural characteristics After incubation at 30° C. for 10 days, the following cultural characteristics were observed.

| Medium | Condition and color of aerial mycelium | Vegetative mycelium reverse color | Diffusible pigment |
|---|---|---|---|
| Sucrose-nitrate agar | No aerial growth | Pale yellow, small colonies | Pink |
| Glucose-Asparagine agar | Light gray to grayish, cottony | Pale yellow brown, small colonies | Orange |
| Glycerin-Asparagine agar | Light gray, powdery | Pale yellow to pale yellow brown, folded | Pale orange |
| Starch-inorganic salt agar | Light gray, powdery to floccose | Yellow brown to olive gray, small colonies | None |
| Tyrosine agar | Light gray to gray white, powdery to floccose | Yellow brwon, folded | Reddish orange |
| Nutrient agar | No aerial growth | Colorless to pale yellow, small colonies | None |
| Yeast malt extract agar | White to gray white, powdery | Pale yellow to pale yellow brown, folded | None |
| Oatmeal agar | Light gray to gray, powdery to floccose | Colorless to pale yellow, small colonies | Dull orange |
| Peptone-yeast iron agar | No aerial growth | Colorless to cream, small colonies | None |
| Bennett's agar | Gray, powdery to floccose | Pale yellow brown, slightly folded orange | Dull reddish |
| Glucose-peptone-gelatin | No aerial growth | Colorless to pale yellow, folded | None |
| Skim milk | No aerial growth | Scanty growth | None |

The diffusible pigment produced in media changes its shade in response to changes in pH, assuming a yellow color on dropwise addition of 0.05N-HCl and a red color on dropwise addition of 0.05N-NaOH.

(iii) Physiological characteristics (1) Temperature range of growth (on Bennet's agar medium): 15°–40° C., optimal 28° C.
(2) Liquefaction of gelatin (glucose peptone agar): Negative
(3) Hydrolysis of starch (starch-inorganic salt agar): Pisitive
(4) Coagulation of milk: Negative
(5) Peptonization of milk: Negative
(6) Production of melanoid pigments (tyrosine agar, peptone-yeast-iron agar, and tryptone yeast broth): Negative
(7) Assimilation of carbon sources (Pridham and Gottlieb agar):
L-Arabinose: +
Cellulose: −
D-Fructose: +
Galactose: +
Glucose: +
Glycerin: +
Inositol: −
Lactose: −
Maltose: +
D-Mannitol: +
Mannose: +
Raffinose: ±
L-Rhamnose: +
Salicin: ±
Sucrose: +
D-Xylose: ±
(+: well assimilated; ±: slightly assimilated; −: not assimilated)

Based on the above test results it is clear that the No. 5995 strain belongs to the genus Streptomyces. The characteristics of the strain may be summarized as follows.
(1) The morphology of aerial mycelium is monopodially spiral.
(2) The spore surface is smooth.
(3) The surface color of growth is light gray.
(4) The vegetative mycelium is pale yellow-yellow brown.
(5) Non-chromogenic; produces a pigment in the orange series, which varies with pH of the medium.
(6) Only weakly proteolytic
(7) Strongly hydrolyzes starch.
(8) Ferments a broad range of carbon sources other than inositol and salicin.

Reference to Bergey's Manual of Determinative Bacteriology VIII (1974); E. B. Shirling and D. Gottlieb, ISP (International Streptomyces Project) Reports, International Journal of Systematic Bacteriology, Vol. 18, pp. 69 & 279 (1968), ditto Vol. 19, p. 391 (1969) and ditto Vol. 22, p. 265 (1972); S. A. Waksman, the Actinomycetes, Vol. 2; and other recent literature on newly discovered species for known organisms which might have characteristics similar to those described hereinbefore did not turn out any known such species. Though the following species appear to be somewhat akin to the No. 5995 strain, there are differences, as set forth below.

(1) *Streptomyces minoensis*
The aerial mycelium is in many cases flexuous to hooks. Substantially, no production of soluble pigments. Inositol is utilized well.

(2) *Streptomyces saraceticus*
No production of soluble pigments. The vegetative mycelium does not produce pH-dependent pigments. Rhamnose is not utilized.

(3) *Streptomyces erythrogriseus*
The aerial mycelium may assume a color in the red-White series on glycerin asparagine agar. Neither sucrose nor raffinose is utilized. Inositol is utilized.

(4) *Streptomyces griseroaurantiacus*
The soluble pigment discolors from orange to red in the presence of HCl and to brown under the influence of NaOH. Inositol is utilized. Sucrose is not utilized.

The above comparative investigation did not turn out any microorganism, among those hithereto known, which would produce a diffusible pigment variable from yellow to orange to red in response to changes of pH, which is the most outstanding feature of the No. 5995 strain, nor was found any know microorganism showing a carbohydrate assimilation spectrum similar to that of the No. 5995 strain. Based on these and other findings, it seems appropriate to conclude that the No. 5995 strain belongs to a new species of microorganism.

In consideration of the orange shade of the diffusible pigment characterizing this strain, the No. 5995 strain was designated *Streptomyces auranticolor* No. 5995.

The No. 5995 strain has been deposited with Fermentation Research Institute of the Agency of Industrial Technology at 1–3, Higashi 1-chome, Yatabe-cho, Tsukuba-gun, Ibaragi Prefecture under FERM-P No. 5365 (Filed Feb. 27, 1980). The (Ia)-producing strain of the genus Stremptomyces which is exploited in the practice of this invention can be used after an enhancement of its (Ia)-producing ability by a mutagenic treatment which is known per se, e.g. irradiation with ultraviolet light, X-rays, etc., treatment with a chemical mutagen such as N-methyl-N'-nitro-N-nitrosoguanidine (NTG) or 2-aminopurine, or conjugation.

Production of compound (Ia) by the cultivation of a (Ia)-producing Streptomyces strain can as a rule be conducted by the general fermentation methods but a submerged culture method using a liquid medium is generally advantageous. The medium may be synthetic, semisynthetic or natural, and may be composed of such carbon sources as glucose, sucrose, glycerin, dextrin, starch, etc. and such nitrogen sources, organic or inorganic, as meat extract, peptone, casein hydrolysate, gluten meal, corn meal, cottonseed cake, soybean meal, corn steep liquor, dried yeast, aluminum sulfate, ammonium phosphate, urea, etc. In addition, metal carbonates, such as calcium carbonate, metal phosphates such as potassium dihydrogen phosphate, potassium monohydrogen phosphate, etc., and metal chlorides such as magnesium chloride may be added to the medium in suitable proportions. If copious foaming is encountered during fermentation, there may be added an antifoam such as higher alcohols, vegetable oils, silicon compounds, etc. Among these antifoams, vegetable oils can be exploited also as sources of carbon. The incubation temperature within the range of about 25° to 30° C. is generally suitable, and satisfactory results are often obtained if seed culture or preincubation is performed when large-scale fermentation is undertaken. The cultivation time is suitably about 50 to 100 hours, and a longer incubation time may be used when the medium concentration is high.

The above-mentioned culture conditions are only typical and an optimum set of conditions should of course be chosen in accordance with characteristics of the particular strain used.

The compound (I) is produced extracellularly for the most part and, therefore, is harvested and purified by usual procedures for the production of antibiotics in general, i.e. removal of cells by centrifugation or filtration and subsequent recovery from the supernatant or filtrate. Thus, concentration under reduced pressure, lyophilization, solvent extraction, pH adjustment, treatment with resins, e.g. anion exchange resins, cation exchange resins or noionic adsorption resins, treatment with adsorbents such as activated carbon, silicon dioxide, silica gel, cellulose, alumina, etc., crystallization, recrystallization, etc. are carried out singly, in a suitable combination or sequence, or in repetition so as to isolate, separate and purify the active compound.

The compound (Ia) can thus be produced by cultivating the (Ia)-producing microorganism and harvesting the elaboration product (Ia) in the per se conventional manner. The harvesting and purifying stage of the process will be explained below by way of illustration.

The compounds (Ia) may be represented by the following specific formulas.

The formula (Ia-A) represents the compound of formula (Ia) wherein $R^1$ and $R^2$ taken together mean

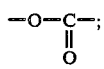

The formula (Ia-B) represents the compound of formula (Ia) wherein $R^1$ is hydrogen and $R^2$ is carboxy;

The formula (Ia-C) represents the compound (Ia) wherein $R^1$ is hydroxy and $R^2$ is carboxy.

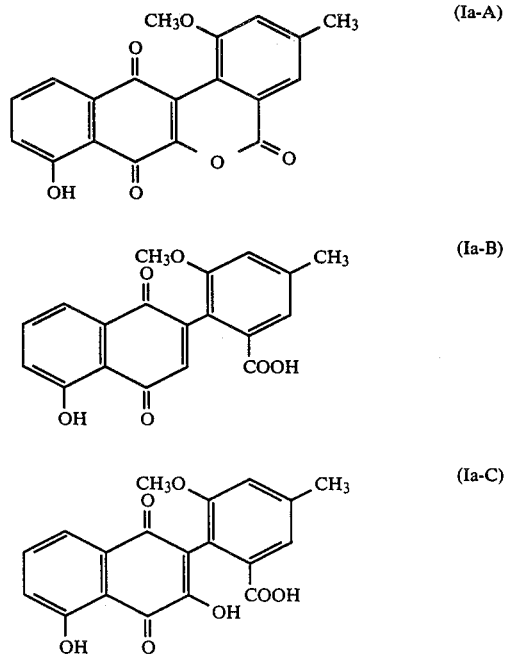

Many of the (Ia)-producing microorganisms of the genus Streptomyces elaborate all of (Ia-A), (Ia-B) and (Ia-C) simultaneously but they may produce only one or two of these compounds selectively according to the particular strain or/and cultural conditions.

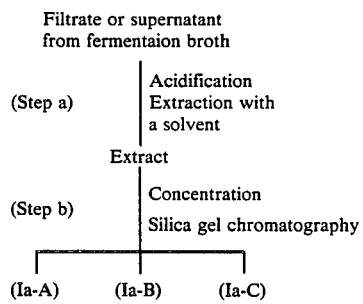

Step a:
The fermentation broth is first acidified in the conventional manner, i.e. preferably brought to pH about 2 with hydrochloric acid, and then, the active compound is extracted with ethyl acetate, butyl acetate or chloroform, preferably with ethyl acetate.

Step b:
The extract obtained in Step a is concentrated under reduced pressure and subjected to chromatography on an adsorbent such as silica gel. When silica gel is used as the adsorbent, serial elution may be carried out with benzene, benzene-ethyl acetate (3:1), and benzene-ethyl acetate (1:1). The desired compounds (Ia-A), (Ia-B) and (Ia-C), then, emerge respectively in the corresponding fractions. It will be obvious to those skilled in the art that selection of suitable adsorbents or/and solvent systems for this kind of procedure is a routine work for chemists and chemical engineers and, therefore, that this invention is not limited to the above exemplary description. The desired compounds (Ia-A), (Ia-B) and (Ia-C) can be isolated and separated in the above manner but as aforesaid, (Ia-C) can be converted to (Ia-A) by reaction with acetic anhydride, trifluoroacetic anhydride or the like. Since (Ia-A) is readier to crystallize than (Ia-C), the extract obtained in Step a can be reacted with a dehydrating agent such as an organic acid anhydride (e.g. acetic anhydride, trifluoroacetic anhydride) so as to convert (Ia-C) therein to (Ia-A) and, then, subjected to silica gel column chromatography so as to obtain (Ia-A) and (Ia-B).

The desired compounds (Ia-B) and (Ia-C) can also be obtained as salts by treating a solution or concentrate containing (Ia-B) and (Ia-C) with a base (for example, inorganic bases such as potassium hydroxide, ammonia, etc. and organic bases such as triethylamine, ethanolamine, dicyclohexylamine, etc.) at an optional stage in the production process, e.g. at the stage of extraction, isolation or purification. The compounds (Ia-B) and (Ia-C) isolated in the free forms can be converted to salts such as those mentioned above by the per se conventional procedures. Conversely, the salt of (Ia-A) or (Ia-B) thus obtained can be converted to the free compound by treating the former with an ion exchange resin, a mineral acid or the like.

(iv) Final compounds (Ia-A), (Ia-B) and (Ia-C):
(i) (Ia-A):
(1) Elemental analysis (%): C, 68.00%, H, 3.53%.
(2) Molecular weight: 336 (based on mass spectrum).
(3) Melting point: 289°–291° C.
(4) Optical rotation: $[\alpha]_D^{25} = 0$.
(5) Ultraviolet absorption spectrum: 242, 303, 426 mµ.
(6) Infrared absorption spectrum: $\nu$(KBr)=3070, 2980, 2940, 1760, 1690, 1640, 1610, 1590, 1580, 1555, 1475, 1455, 1420, 1390, 1384, 1382, 1355, 1328, 1278, 1248, 1228, 1194, 1165, 1140, 1072, 1045, 1015, 984, 961, 945, 922, 895, 888, 865, 828, 815, 790, 785, 780, 745, 730, 720, 710, 702, 698 cm$^{-1}$.

(7) Solubility: Partially soluble in dimethyl sulfoxide and tetrahydrofuran. Sparingly soluble in methanol, ethanol, acetone and chloroform. Insoluble in water.

(8) Color reactions: Positive: potassium permanganate, iodine and ferric chloride. Negative: vanillin.

(9) Stability: Instable in acid and alkaline solutions.

(10) Appearance: Orange-red prisms.

(11) Nuclear magnetic resonance spectrum, DMSO-d$_6$ (ppm): 2.38(3H, s), 3.68(3H, s), 7.12(1H, s), 7.30(1H, dd, J=7.6 Hz, 1.3 Hz). 7.38(1H, s), 7.50(1H, dd, J=7.6 Hz, 1.3 Hz), 7.74(1H, t, J=7.6 Hz), 11.4(1H, br.).

Based on the above physico-chemical properties and the results of other investigations, the compound (Ia-A) was identified to have the structural formula given hereinbefore.

(ii) (Ia-B):

(1) Elemental analysis: C, 67.32%; H, 4.34%.

(2) Molecular weight: 338 (based on mass spectrum).

(3) Melting point: ≧300° C.

(4) Optical rotation: $[\alpha]_D^{25} = 0$.

(5) Ultraviolet absorption spectrum: 276, 410 m$\mu$.

(6) Infrared absorption spectrum: $\nu$(KBr)=3500 to 2200(br.) 1720, 1690, 1645, 1610, 1580, 1570(sh.) 1490, 1470, 1453, 1410, 1365, 1322, 1290, 1253, 1222, 1185, 1165, 1110, 1082, 1070, 1050(sh.) 990, 967, 940, 920, 910, 862, 853, 837, 810, 780(sh.) 770, 745, 725, 690, 680, 675(sh.) cm$^{-1}$.

(7) Solubility: Readily soluble in methanol, ethanol, acetone, ethyl acetate and chloroform. Insoluble in water, benzene and hexane.

(8) Color reactions: Positive: potassium permanganate, iodine and ferric chloride. Negative: vanillin.

(9) Stability: Stable for 30 minutes in 50° C. solutions at pH 2 and pH 10.

(10) Appearance: Orange-colored prisms.

(11) Nuclear magnetic resonance spectrum, CDCl$_3$ (ppm): 2.40(3H, s), 3.66(3H, s), 6.78(1H, s), 7.02(1H, s), 7.25(1H, m), 7.68(3H, m), 7.80(1H, br.), 12.00(1H, br. s).

Based on the above physicochemical properties and the results of other investigations, the compound (Ia-B) was identified to have the structural formula given hereinbefore.

(iii) (Ia-C):

(1) Elemental analysis: C, 64.23%; H, 3.91%.

(2) Molecular weight: 354 (based on mass spectrum).

(3) Melting point: 288°–290° C.

(4) Optical rotation: $[\alpha]_D^{25} = 0$.

(5) Ultraviolet absorption spectrum: 288, 412 m$\mu$.

(6) Infrared absorption spectrum: $\nu$(KBr)=3380, 3300 to 2300 (br.), 2920, 2850, 2600, 1690, 1660(sh.), 1645(sh.), 1630, 1608, 1580, 1570(sh.), 1545, 1515, 1490(sh.), 1480, 1460, 1395(sh.), 1385, 1350, 1310, 1290, 1260, 1230, 1215, 1195(sh.), 1190, 1175, 1160, 1105, 1065, 1038, 962, 938, 910, 870, 855, 835, 818, 795, 788, 755, 735, 725, 690 cm$^{-1}$.

(7) Solubility: Readily soluble in methanol and ethanol. Partially soluble in acetone and ethyl acetate. Insoluble in water, ether and hexane.

(8) Color reactions: Positive: potassium permanganate, iodine and ferric chloride. Negative: vanillin.

(9) Stability: Stable for 30 minutes in 50° C. solutions at pH 2 and pH 10.

(10) Appearance: Orange-colored needles.

(11) Nuclear magnetic resonance spectrum, DMSO-d$_6$(ppm): 2.43(3H, s), 3.73(3H, s), 7.17 (1H, s), 7.2 to 7.9(4H, m), 11.63(1H, s), 2.6 to 4.6(2H, br.).

Based on the above physico-chemical properties and the results of other investigations, the compound (Ia-C) was identified to have the structural formula given hereinbefore.

(3) Utility of the product compounds

The 1,4-naphthoquinone derivative (I) of this invention is a very effective anticoccidial agent as will be understood from the test results given below.

(1) A coccidium infection and treatment test in the chicken

TEST EXAMPLE 1

Male white Leghorn chickens, aged 2 weeks and with a mean body weight of 100 g, were treated with two representative examples of product compound (I) and Monensin, a control drug, at the various dose levels indicated in Table 1. Each compound and drug was suspended in a 1% aqueous solution of gum arabic and 2 ml per dose of the suspension was administered 3 times a day for 3 consecutive days. Birds in the untreated control groups were given 2 ml per dose of a 1% aqueous solution of gum arabic only in otherwise the same manner.

Immediately after the first dosing, birds in the infected groups were orally inoculated with $3.0 \times 10^4$/bird of oöcysts of *Eimeria tenella*. Body weights were taken at the first treatment and on the 3rd day after the entire course of treatment to investigate changes in body weight. Immediately after the second taking of body weights, the birds were terminated and autopsied to examine and score the cecal lesions.

TABLE 1

| | Drugs administered and effects | | | | | |
|---|---|---|---|---|---|---|
| | Monensin | | (Ia-A) | | (Ia-B) | |
| Dosage | Lesion score | Weight gain index | Lesion score | Weight gain index | Lesion score | Weight gain index |
| 40 | 0 | 41 | 0 | 95 | 0 | 102 |
| 20 | 0 | 51 | 0 | 108 | 0 | 90 |
| 10 | 0 | 68 | 0 | 106 | 0 | 95 |
| 5 | 2.3 | 98 | 0.3 | 97 | 0 | 80 |
| 2.5 | 2.7 | 92 | 2.0 | 92 | 3 | 68 |
| 1.25 | 4.0 | 99 | 2.0 | 108 | | |
| Non-treated group | 4.0 | 69 | 4.0 | 69 | 4.0 | 65 |
| Non-infected group | 0 | 100 | 0 | 100 | 0 | 100 |

Dosage: The total dose (mg) given to each bird during the test period.
Lesion score: 0 - Very effective (no pathological change)
1 - Effective
2 - Slightly effective
3 - Not effective
4 - Not effectetive (copious hemmorrhage in the cecum)
Weight gain index: These indices were computed with the body weight gain of birds in the non-infected group being taken as 100.

Three birds were assigned to each of the infected-non-treated groups, non-infected groups, the monencin group and the (Ia-A) groups, and the weight gain indices were computed from the mean body weight values for 3 birds. The (Ia-B) groups each consisted of a bird only.

It will be apparent from the above test results that the 1,4-naphthoquinone derivative (I) of this invention is of value as an anticoccidial agent. As an anticoccidial drug, the compound (I) can be employed alone but, more generally, is preferably administered in admixture with a vehicle such as solvent-extracted rice bran, solvent-extracted soybean meal, wheat bran, kaolin, talc, calcium carbonate, lactose, water, etc. or dietarily along with feedstuffs, that is to say after incorporating the compound (I) or said mixture in feedstuffs. The 1,4-naphthoquinone derivative (I) in such applications need not be a pure preparation but when the derivative (I) has been obtained by fermentation, the fermentation broth as such or partially purified products such as the cells or mycelia, the supernatant or filtrate, and so on may also be employed with advantage.

While the proper dosage of the anticoccidial agent according to this invention varies with different species of animals, stages of growth and other factors, the optimum dosage is selected usually from the range of 1 to 100 mg/kg/day.

The following examples are intended to illustrate this invention in further detail.

(A) METHODS OF SYNTHESIS

Example 1

Synthesis of 8-hydroxy-1-methoxy-3-methyl-7,12-dihydro-5H-benzo[d]naphtho[2,3-b]pyran-5,7,12-trione (1) Synthesis of N-(1,1-dimethyl-2-hydroxy)-2,3-dimethoxy-5-methylbenzamide In methylene chloride (120 ml) was dissolved 2,3-dimethoxy-5-methylbenzoic acid (15.7 g) followed by addition of triethylamine (8.9 g). The mixture was cooled on an ethanol-dry ice bath, and under stirring, ethyl chloroformate (8.6 g) was added. The mixture was further stirred at that temperature for an hour, after which 2-amino-2-methylpropanol (9.6 g) was added. Then, at room temperature, the mixture was further stirred for 7 hours. The reaction mixture was then washed with dilute HCl and dilute sodium carbonate solution in succession and dried over magnesium sulfate. The solvent was distilled off and the residual colorless oil was crystallized from diethyl ether-hexane to give colorless needles (19.2 g).

m.p. 73°–75° C.

Elemental analysis ($C_{14}H_{21}NO_4$) (%): Found C, 62.62; H, 8.01; N, 5.24; Calcd. C, 62.90; H, 7.92; N, 5.24.

(2) 2-(2,3-Dimethoxy-5-methylphenyl)-4,4-dimethyl-2-oxazoline

In diethyl ether (150 ml) was dissolved N-(1,1-dimethyl-2-hydroxy)-2,3-dimethoxy-5-methylbenzamide(19.2 g) as obtaiend in (1), and while the solution was stirred at room temperature, thionyl chloride (21 ml) was added dropwise. The mixture was stirred at the same temperature for 15 minutes, after which the diethyl ether was decanted off. The residue was washed with diethyl ether (30 ml×5), 20% aqueous sodium hydroxide was added, and the mixture was extracted with diethyl ether. The solvent layer was washed with water and dried over magnesium sulfate. The solvent was then distilled off and the residue was further distilled under reduced pressure to give a colorless oil (14.3 g).

b.p. 124°–125° C./2 mmHg

Elemental analysis ($C_{14}H_{19}NO_3$) (%): Found C, 67.1; H, 7.8; N, 5.6; Calcd. C, 67.4; H, 7.7; N, 5.6.

(3) Synthesis of 2-(2-amino-3-methoxy-5-methylphenyl)-4,4-dimethyl-2-oxazoline

In dry tetrahydrofuran (80 ml) was dissolved 2-(2,3-dimethoxy-5-methylphenyl)-4,4-dimethyl-2-oxazoline (5 g). After addition of lithium amide (60 g), the mixture was stirred in a nitrogen gas stream at room temperature for 3 days. To the reaction mixture was added ice-water, followed by extraction with diethyl ether. The solvent layer was washed with water and dried over magnesium sulfate. The solvent was then distilled off to give a brown oil. This oil was chromatographed on silica gel to give colorless prisms (1.2 g) of 2-(2-amino-3-methoxy-5-methylphenyl)-4,4-dimethyl-2-oxazoline. m.p. 135°–137.5° C. (crystallized from diethyl ether)

Elemental analysis ($C_{13}H_{18}N_2O_2$) (%): Found C, 66.37; H, 7.75; N, 11.80; Calcd. C, 66.64; H, 7.74; N, 11.96.

(4) Synthesis of 2-amino-3-methoxy-5-methylbenzoic acid

In 10% HCl (42 ml) was dissolved 2-(2-amino-3-methoxy-5-methylphenyl)-4,4-dimethyl-2-oxazoline (500 mg) and the solution was refluxed for 14 hours. The reaction mixture was concentrated to about 10 ml and adjusted to pH 4.6–4.8 with aqueous ammonia. The resultant crystalline precipitate was extracted with ethyl acetate and dried over magnesium sulfate. The solvent was then distilled off and the residual crude crystals (250 mg) were recrystallized from ethanol-water to give colorless needles.

m.p. 170°–172° C. Elemental analysis ($C_9H_{11}NO_3$) (%): Found C, 59.56; H, 6.02; N, 7.75; Calcd. C, 59.66; H, 6.12; N, 7.73.

(5) Synthesis of 2-(3,5-dihydroxy-1,4-naphthoquinon-2-yl)-3-methoxy-5-methylbenzoic acid In an aqueous solution of hydrogen chloride (conc. HCl:water=0.15 ml:4 ml) was dissolved 2-amino-3-methoxy-5-methylbenzoic acid (170 mg), and under cooling with a freezing agent and ice, an aqueous solution (4 ml) of sodium nitrate was added dropwise. The resultant diazonium salt was added dropwise to a solution of hyroxyjuglone (180 mg) in 5% aqueous potassium hydroxide (10 ml) at a temperature of 40°–45° C. The mixture was stirred at that temperature for an hour, after which it was allowed to cool, acidified with HCl and extracted with ethyl acetate. The extract was washed with water and dried over magnesium sulfate. The solvent was distilled off to give 2-(3,5-dihydroxy-1,4-naphthoquinon-2-yl)-3-methoxy-5-methylbenzoic acid.

(6) Synthesis of 8-hydroxy-1-methoxy-3-methyl-7,12-dihydro-5H-benzo[d]naphtho[2,3-b]pyran-5,7,12-trione The entire amount of the 2-(3,5-dihydroxy-1,4-naphthoquinon-2-yl)-3-methoxy-5-methylbenzoic acid obtained above was dissolved in ethyl acetate (10 ml) and while the solution was stirred at room temperature, a mixture (1 ml:10 ml) of trifluoroacetic anhydride and acetic anhydride was added. The mixture was further stirred at the same temperature for an hour. This reaction mixture was washed with water and dilute aqueous sodium carbonate in that order, followed by drying over magnesium sulfate. The solvent was then distilled off and the residual brown oil was subjected to silica gel column chromatography to give vermillion-colored crystals (20 mg).

m.p. 282°–292° C.

In infrared and magnetic resonance spectra and other physical constants, the above product was in complete agreement with the product obtained by fermentation in Example 15.

Example 2

Synthesis of 8-hydroxy-1-methoxy-3-methyl-7,12-dihydro-5H-benzo[d]naphtho[2,3-b]pyran-5,7,12-trione (1) Synthesis of 2-(5-hydroxy-2,3-epoxy-1,4-dihydronaphthalene-1,4-dion-2-yl)-3-methoxy-5-methylbenzoic acid In methanol (15 ml) was dissolved 2-(5-hydroxy-1,4-naphthoquinon-2-yl)-3-methoxy-5-methylbenzoic acid (100 mg) as obtained in Example 15, followed by addition of sodium hydrogen carbonate (80 mg). The mixture was stirred under ice-cooling. Then, 30% hydrogen peroxide (1.5 ml) was added dropwise and the reaction mixture was allowed to return gradually to room temperature, at which temperature it was further stirred for 5 hours. The solvent was then distilled off under reduced pressure, dilute HCl was added to the residue and the mixture was extracted with ethyl acetate. The extract was dried by addition of magnesium sulfate and the solvent was distilled off to give 2-(5-hydroxy-2,3-epoxy-1,4-dihydronaphthalene-1,4-dion-2-yl)-3-methoxy-5-methylbenzoic acid (100 mg).

m.p. 267°–268° C.

(2) Synthesis of 8-hydroxy-1-methoxy-3-methyl-7,12-dihydro-5H-benzo[d]naphtho[2,3-b]pyran-5,7,12-trione In methylene chloride (20 ml) was dissolved 2-(5-hydroxy-2,3-epoxy-1,4-dihydronaphthalene-1,4-dion-2-yl)-3-methoxy-5-methylbenzoic acid (100 mg) as obtained in (1), followed by addition of boron trifluoride (1 ml) under ice-cooling and stirring. The mixture was stirred at that temperature for an hour, after which it was allowed to return gradually to room temperature. The mixture was then stirred at room temperature overnight. The reaction mixture was poured in ice-water and extracted with ethyl acetae. The extract was washed with water and dried over magnesium sulfate. The solent was then distilled off and the residue was chromatographed on silica gel and eluted with chloroform to give crystals (60 mg) of 8-hydroxy-1-methoxy-3-methyl-7,12-dihydro-5H-benzo[d]naphtho[2,3-b]pyran-5,7,12-trione. The physicochemical properties of this compound were in complete agreement with those of the product obtained in Example 15.

Example 3

Synthesis of methyl 2-(3-methoxy-5-hydroxy-1,4-naphthoquinon-2-yl)-3-methoxy-5-methylbenzoate 2-(3,5-Dihydroxy-1,4-naphthoquinon-2-yl)-3-methoxy-5-methylbenzoic acid (100 mg) was dissolved in methanol (20 ml) and treated with diazomethane at room temperature. After 2 hours of reaction, the excess diazomethane was decomposed with acetic acid, the solvent was distilled off under reduced pressure, and the residue was subjected to silica gel column chromatography, elution being carried out with chloroform. The above procedure gave methyl 2-(3-methoxy-5-hydroxy-1,4-naphthoquinon-2-yl)-3-methoxy-5-methylbenzoate (60 mg).

m.p. 165°–167° C.

Example 4

Synthesis of methyl 2-(3,5-dimethoxy-1,4-naphthoquinon-2-yl)-3-methoxy-5-methylbenzoate In chloroform (10 ml) was dissolved methyl 2-(3-methoxy-5-hydroxy-1,4-naphthoquinon-2-yl)-3-methoxy-5-methylbenzoate (50 mg) as obtained in Example 3, followed by addition of silver oxide (200 mg) and methyl iodide (3 ml). The mixture was refluxed with stirring for 5 hours. After insolubles were filtered off, the solvent was distilled off under reduced pressure. The residue was subjected to silica gel column chromatography using chloroform as the eluent. The eluate was concentrated and crystallized from methanol. The above procedure gave crystals (20 mg) of methyl 2-(3,5-dimethoxy-1,4-naphthoquinon-2-yl)-3-methoxy-5-benzoate.

m.p. 148°–150° C.

Example 5

Synthesis of 4-chloro-8-hydroxy-1-methoxy-3-methyl-7,12-dihydro-5H-benzo[d]naphtho[2,3-b]pyran-5,7,12-trione (1) Synthesis of methyl 2-(3,5-dihydroxy-1,4-naphthoquinon-2-yl)-3-methoxy-5-methyl-6-chlorobenzoate 8-Hydroxy-1-methoxy-3-methyl-7,12-dihydro-5H-benzo[d]naphtho[2,3-b]pyran-5,7,12-trione (400 mg) as prepared in Example 1 was dissolved in a 20:100:1 mixture (20 ml) of acetic acid, methylene chloride and methanol, followed by addition of sulfuryl chloride (2 ml). The mixture was refluxed for 5 hours. The solvent was distilled off under reduced pressure and the residue was subjected to silica gel column chromatography to give methyl 2-(3,5-dihydroxy-1,4-naphthoquinon-2-yl)-3-methoxy-5-methyl-6-chlorobenzoate.

(2) In 20% aqueous sodium hydroxide was dissolved methyl 2-(3,5-dihydroxy-1,4-naphthoquinon-2-yl)-3-methoxy-5-methyl-6-chlorobenzoate as obtained in (1) and the solution was refluxed for 3 hours. The reaction mixture was allowed to cool, acidified, and extracted with ethyl acetate. The solvent layer was washed with water and dried. The solvent was then distilled off and the residue was dissolved in tetrahydrofuran (2 ml). After addition of acetic anhydride (2 ml), the crystals that separated out were recovered by filtration, washed with diethyl ether and dried to give crystals (70 mg) of 4-chloro-8-hydroxy-1-methoxy-3-methyl-7,12-dihydro-5H-benzo[d]naphtho[2,3-b]pyran-5,7,12-trione.

m.p. 294°–296° C.

Example 6

Synthesis of 1,8-dihydroxy-3-methyl-7,12-dihydro-5H-benzo[d]naphtho[2,3-b]pyran-5,7,12-trione In methylene chloride was dissolved 8-hydroxy-1-methoxy-3-methyl-7,12-dihydro-5H-benzo[d]naphtho[2,3-b]pyran-5,7,12-trione (2 g), and under ice-cooling, a methylene chloride solution of boron tribromide (2 ml) was added dropwise. The mixture was further stirred at that temperature for 2 hours, at the end of which time it was washed with water and dried over magnesium sulfate. The solvent was then distilled off to give crude crystals. Recrystallization from methanol gave yellow crystals (1.1 g). m.p. 236°–238° C.

Example 7

Synthesis of methyl 2-(5-hydroxy-1,4-naphthoquinon-2-yl)-3-methoxy-5-methylbenzoate In methanol (50 ml) was dissolved 2-(5-hydroxy-1,4-naphthoquinon-2-yl)-3-methoxy-5-methylbenzoic acid (1 g) as obtained in Example 15, followed by addition of a diethyl ether solution of diazomethane (20 ml). The mixture was allowed to stand at room temperature for an hour, after which the diethyl ether and methanol were distilled off. The residue was subjected to silical gel chromatography and recrystallized from diethyl ether-n-hexane. The procedure yielded yellow crystals (500 mg) of methyl 2-(5-hydroxy-1,4-naphthoquinon-2-yl)-3-methoxy-5-methylbenzoate.
m.p. 140°-143° C.

Example 8

Synthesis of N-cyclohexyl-N-[(N'-cyclohexyl)carbamoyl]-2-(5-hydroxy-1,4-naphthoquinon-2-yl)-3-methoxy-5-methylbenzamide In methylene chloride was dissolved 2-(5-hydroxy-1,4-naphthoquinon-2-yl)-3-methoxy-5-methylbenzoic acid (338 mg), and under ice-cooling and stirring, N,N'-dicyclohexylcarbodiimide was added portionwise. The mixture was stirred at room temperature for a day, after which the solvent was distilled off under reduced pressure. The residue was subjected to column chromatography on silica gel and crystallized from petroleum ether. The procedure gave 200 mg of N-cyclohexyl-N-[(N'-cyclohexyl)carbamoyl]-2-(5-hydroxy-1,4-naphthoquinon-2-yl)-3-methoxy-5-methylbenzamide as red crystals.
m.p. 187°-190° C.

Example 9

Synthesis of diethyl 1-[2-(5-hydroxy-1,4-naphthoquinon-2-yl)-3-methoxy-5-methylbenzamido]ethylphosphonate In methylene chloride was dissolved 2-(5-hydroxy-1,4-naphthoquinon-2-yl)-3-methoxy-5-methylbenzoic acid (1.5 g) as obtained in Example 15 together with diethyl 1-aminoethylphosphonate, followed by addition of N,N'-dicyclohexylcarbodiimide in portions at room temperature. The mixture was stirred at that temperature overnight and the byproduct dicyclohexylurea was filtered off. The solvent was distilled off and the residue was subjected to silica gel column chromatography. Crystallization from diethyl ether-n-hexane gave yellow crystals (1 g) of diethyl 1-[2-(5-hydroxy-1,4-naphthoquinon-2-yl)-3-methoxy-5-methylbenzamido]ethylphosphonate. m.p. 130°-132° C.

Example 10

Synthesis of 1-[2-(5-hydroxy-1,4-naphthoquinon-2-yl)-3-methoxy-5-methylbenzamido]ethylphosphonic acid Trimethylsilyl bromide was added to diethyl 1-[2-(5-hydroxy-1,4-naphthoquinon-2-yl)-3-methoxy-5-methylbenzamido]ethylphosphonate (500 mg) as obtained in Example 9 and the mixture was stirred at room temperature for 2 hours. The excess trimethylsilyl bromide was distilled off, water was added to the residue, and the mixture was stirred at room temperature for 30 minutes. The resultant crude crystals were recovered by filtration and recrystallized from methanol. The above procedure gave yellow crystals (200 mg) of 1-[2-(5-hydroxy-1,4-naphthoquinon-2-yl)-3-methoxy-5-methylbenzamido]ethylphosphonic acid.
m.p. $\geq$ 300° C.
IR: $\nu$(Nujol)=3600 to 2500, 1665, 1638, 1620, 1607, 1580, 1510 cm$^{-1}$.

Example 11

Synthesis of 2-[3-(p-tolylphenylthio)-5-hydroxy-1,4-naphthoquinon-2-yl]-3-methoxy-5-methylbenzoic acid In ethanol was suspended 2-(5-hydroxy-1,4-naphthoquinon-2-yl)-3-methoxy-5-methylbenzoic acid (130 mg) as obtained in Example 15, and under stirring at room temperature, a solution of 4-methylbenzenethiol (80 mg) in ethanol was added. The mixture was stirred at that temperature for 30 minutes, after which the ethanol was distilled off under reduced pressure. The residue was subjected to silica gel chromatography and recrystallized from diethyl ether-n-hexane to give yellow crystals (60 mg) of 2-[3-(p-tolyphenylthio)-5-hydroxy-1,4-naphthoquinon-2-yl]-3-methoxy-5-methylbenzoic acid. m.p. 96°-98° C.

Example 12

Synthesis of methyl 2-[2-(5-hydroxy-1,4-naphthoquinon-2-yl)-3-methoxy-5-methylbenzamido]benzoate 2-(5-Hydroxy-1,4-naphthoquinon-2-yl)-3-methoxy-5-methylbenzoic acid (300 mg), obtained in Example 15, and methyl anthranylate (300 mg) were dissolved in dry methylene chloride (15 ml). Under ice-cooling and stirring, dicyclohexylcarbodiimide (206 mg) was added. The mixture was stirred at that temperature for an hour and, then, further stirred at room temperature overnight. The insolubles were filtered off and the filtrate was washed with dilute HCl, water and dilute aqueous sodium carbonate, and dried over anhydrous sodium sulfate. The solvent was distilled off and the residue was subjected to silica gel column chromatography using chloroform as the eluent, followed by recrystallization from methanol. The procedure gave crystals (250 mg) of methyl 2-[2-(5-hydroxy-1,4-naphthoquinon-2-yl)-3-methoxy-5-methylbenzamido]benzoate.
m.p. 190°-194° C.

Example 13

Synthesis of 8-acetoxy-1-methoxy-3-methyl-7,12-dihydro-5H-benzo[d]naphtho[2,3-b]pyran-5,7,12-trione In pyridine (10 ml) was dissolved 8-hydroxy-1-methoxy-3-methyl-7,12-dihydro-5H-benzo[d]naphtho[2,3-b]pyran-5,7,12-trione (150 mg) as obtained in Example 15, followed by addition of acetic anhydride (5 ml). The mixture was allowed to stand overnight. The solvent was then distilled off under reduced pressure and the residue was extracted with chloroform. The solvent layer was washed with dilute HCl and water, and dried over sodium sulfate. The solvent was distilled off and the residue was crystallized from diethyl ether to give crystals (45 mg) of 8-acetoxy-1-methoxy-3-methyl-7,12-dihydro-5H-benzo[d]naphtho[2,3-b]pyran-5,7,12-trione.
m.p. 267°-269° C.

Example 14

Synthesis of methyl 2-(3-methoxy-5-acetoxy-1,4-naphthoquinon-2-yl)-3-methoxy-5-methylbenzoate In pyridine (3 ml) was dissolved methyl 2-(3-methoxy-5-hydroxy-1,4-naphthoquinon-2-yl)-3-methoxy-5-methylbenzoate (20 mg) as obtained in Example 3, followed by addition of acetic anhydride (3 ml). The mixture was allowed to stand at room temperature overnight. After addition of water, the mixture was extracted with ethyl acetate. The solvent layer was washed with dilute HCl, water and dilute aqueous sodium hydrogen carbonate in that order, and dried over magnesium sulfate. The solvent was then distilled off and the residue was crystallized by addition of methanol. The above procedure gave methyl 2-(3-methoxy-5-acetoxy-1,4-naphthoquinon-2-yl)-3-methoxy-5-methylbenzoate (13 mg).
m.p. 127°-128° C.

(B) FERMENTATION METHODS

Example 15

Production of 8-hydroxy-1-methoxy-3-methyl-7,12-dihydro-5H-benzo[d]naphtho[2,3-b]pyran-5,7,12-trione and 2-(5-hydroxy-1,4-naphthoquinon-2-yl)-3-methoxy-5-methylbenzoic acid A liquid medium composed of 1% soluble starch, 1% glycerin, 1% cottonseed cake, 1% yeast extract and 96% water was distributed into 250 ml Sakaguchi flasks at the rate of 80 ml per flask and sterilized at 120° C. for 20 minutes. Each flask was then inoculated with a loopful of a slant culture of *Streptomyces auranticolor* No. 5995 and incubated under shaking at 30° C. for 3 days. Separately, a 30-liter jar fermentor was filled with 20 l of the same medium as above and sterilized at 120° C. for 20 minutes. Then, the jar was inoculated with 200 ml of the above culture from Sakaguchi flasks and incubated at 30° C. for 2 days, under sparging with 20 l of sterile air per minute and rotary shaking at 300 r.p.m. Separately, a 2,000-liter fermentation tank was charged with 1,750 l of a culture medium composed of 2% soluble starch, 0.5% cottonseed cake, 0.5% wheat germs, 0.25% dried yeast, 0.25% corn steep liquor, 0.05% potassium dihydrogen phosphate, 0.05% of sodium monohydrogen phosphate.12H$_2$O and 96.4% water, and incubated at 120° C. for 20 minutes. The tank was then inoculated with 52.5 l of the culture from the above-mentioned jar fermentor and incubated at 27° C. for 3 days, under sparging with 1.750 ml of sterile air per minute and agitation at 200 r.p.m. After the cultivation was complete, 20 kg of diatomaceous earth was added to the culture broth and the mixture was filtered to give 1,400 l of filtrate. This filtrate was concentrated to 250 ml at a liquid temperature of 30° C. To this concentrate was added 300 l of ethyl acetate and after stirring, the ethyl acetate layer was taken. The above procedure was repeated a second time and the ethyl acetate layers were combined and concentrated to 1 liter. The above concentrate was subjected to silica gel (Merck, 70–230 mesh) column chromatography. Elution was carried out with 8 l of benzene, 8 l of benzene-ethyl acetate (3:1), 2 l of acetone and 8 l of methanol in the order mentioned. The benzene fractions were pooled and concentrated to recover 1.5 g crude crystals of 8-hydroxy-1-methoxy-3-methyl-7,12-dihydro-5H-benzo[d]naphtho[2,3-b]pyran-5,7,12-trione. The crude crystals were recrystallized from tetrahydrofuran to give 1 g of crystals of 8-hydroxy-1-methoxy-3-methyl-7,12-dihydro-5H-benzo[d]-naphtho[2,3-b]pyran-5,7,12-trione.

Then, the benzene-ethyl acetate (3:1) fractions were pooled and concentrated to give 6.5 g crude crystals of 2-(5-hydroxy-1,4-naphthoquinon-2-yl)-3-methoxy-5-methylbenzoic acid. Recrystallization of this product from ethanol yielded 4.2 g crystals of 2-(5-hydroxy-1,4-naphthoquinon-2-yl)-3-methoxy-5-methylbenzoic acid.

Example 16

Production of 2-(3,5-dihydroxy-1,4-naphthoquinon-2-yl)-3-methoxy-5-methylbenzoic acid A 2,000-liter fermentation tank was charged with 1,750 l of a culture medium composed of 2% soluble starch, 0.5% cottonseed cake, 0.5% of wheat germs, 0.25% of dried yeast, 0.25% corn steep liquor, 0.5% potassium dihydrogen phosphate, 0.5% sodium monohydrogen phosphate.12H$_2$O and 96.5% water, and sterilized at 120° C. for 20 minutes. The tank medium was then inoculated with 30 l of a culture prepared by exactly the same procedure as the jar culture of Example 15 and incubated at 25° C. for 3 days, under sparging 1,750 l of sterile air per minute and agitation at 200 r.p.m.

After the cultivation was complete, 20 kg of diatomaceous earth was added and the mixture was filtered to give 1,450 l of filtrate. This filtrate was concentrated to 310 l under reduced pressure and at a liquid temperature not over 30° C. The concentrate was adjusted to pH 2 with 6N HCl and extracted twice with 300 l and 360 l, respectively, of ethyl acetate. The ethyl acetate layers were combined, dried by addition of anhydrous magnesium sulfate and concentrated to give an oil. This oil was dissolved in 200 ml of ethanol, followed by addition of ethyl ether, whereby 5 g of 2-(3,5-dihydroxy-1,4-naphthoquinon-2-yl)-3-methoxy-5-methylbenzoic acid was obtained as a precipitate. This precipitate was dissolved in tetrahydrofuran under heating and the solution was concentrated and cooled to give 3.37 g crystals of 2-(3,5-dihydroxy-1,4-naphthoquinon-2-yl)-3-methoxy-5-methylbenzoic acid.

Example 17

Production of 2-(5-hydroxy-1,4-naphthoquinon-2-yl)-3-methoxy-5-methylbenzoic acid and 8-hydroxy-1-methoxy-3-methyl-7,12-dihydro-5H-benzo[d]naphtho[2,3-b]pyran-5,7,12-trione A 2,000-liter fermentation tank was charged with 1,750 l of a culture medium composed of 2% soluble starch, 0.5% cottonseed cake, 0.5% wheat germs, 0.25% dried yeast, 0.25% corn steep liquor, 0.5% potassium dihydrogen phosphate, 0.5% sodium monohydrogen phosphate.12H$_2$O and 96.5% water, and sterilized at 120° C. for 20 minutes. The tank medium was then inoculated with 30 l of a culture prepared by exactly the same procedure as the jar culture of Example 12 and incubated at 30° C. for 3 days, under sparging with 1,750 l of sterile air per minute and agitation at 200 r.p.m. The broth filtrate (1,700 l) was adjusted to pH 4 and extracted twice with 300 l and 350 l, respectively, of ethyl acetate. The extracts were combined and concentrated to 40 l under reduced pressure. To the concentrate was added a 1% aqueous solution of sodium hydrogen carbonate (30 l) and the mixture was separated into an ethyl acetate layer and an aqueous sodium hydrogen carbonate layer. The ethyl acetate layer was concentrated and subjected to silica gel chromatography, elution being carried out with chloroform. The active fractions were pooled and concentrated, and the concentrate was adsorbed on silica gel and extracted with diethyl ether to remove impurities, whereupon crude crystals of 8-hydroxyl-1-methoxy-3-methyl-7,12-dihydro-5H-benzo[d]naphtho[2,3-b]pyran-5,7,12-trione were obtained. The crude crystals were further subjected to silica gel chromatography using chloroform as the eluent. The eluate was concentrated to give 18.6 g crystals of 2-(5-hydroxy-1,4-naphthoquinon-2-yl)-3-methoxy-5-methylbenzoic acid.

The aqueous sodium hydrogen carbonate layer was adjusted to pH 4 and stirred with 10 l of ethyl acetate. The ethyl acetate layer was taken and concentrated to give an oil. This oil was dissolved in tetrahydrofuran under heating and stirred with 300 ml of acetic anhydride at room temperature for 5 hours to give 22 g crystals of 8-hydroxy-1-methoxy-3-methyl-7,12-dihydro-5H-benzo[d]naphtho[2,3-b]pyran-5,7,12-trione.

We claim:

1. A derivative, including salts of its carboxy function, of the formula

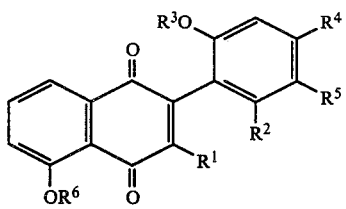

wherein $R^1$ is hydrogen, hydroxy, lower alkoxy, or arylthio; $R^2$ is carboxy; $R^3$ is hydrogen or lower alkyl; $R^4$ is lower alkyl; $R^5$ is hydrogen or halogen; and $R^6$ is hydrogen, lower alkyl, or lower alkanoyl.

2. The derivative of claim 1, wherein $R^1$ is hydrogen; $R^2$ is carboxy; $R^3$ and $R^4$ are lower alkyl; and $R^5$ and $R^6$ are hydrogen.

3. The derivative of claim 1, wherein $R^1$ is hydroxy; $R^2$ is carboxy; $R^3$ and $R^4$ are lower alkyl; and $R^5$ and $R^6$ are hydrogen.

4. The derivative of claim 1 wherein said arylthio is phenylthio, tolylthio, xylylthio, mesylthio, or cumenylthio.

5. A compound, including salts of its carboxy function, of the formula

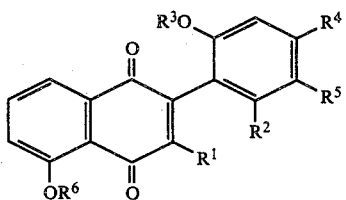

wherein $R^1$ is hydrogen, $R^2$ is carboxy, $R^3$ and $R^4$ are each methyl, and $R^5$ and $R^6$ are each hydrogen.

6. A compound, including salts of its carboxy function, of the formula

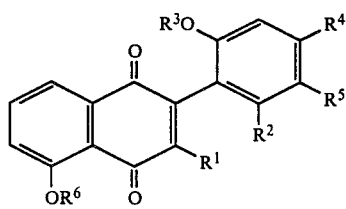

wherein $R^1$ is hydroxy, $R^2$ is carboxy, $R^3$ and $R^4$ are each methyl, and $R^5$ and $R^6$ are each hydrogen.

7. A composition for the treatment of coccidiosis comprising an amount of a derivative of claim 1 which, when administered to a warm blooded animal, will provide an effective amount of said derivative in said animal, and a pharmaceutically acceptable substance.

8. A method of treating coccidiosis comprising administering an effective amount of a derivative of claim 1 to a warm blooded animal.

9. A method of claim 8 wherein said amount is about 1 to about 100 mg/kg of body weight of said animal per day.

10. A method of producing a 1,4-naphthoquinone derivative of the general formula:

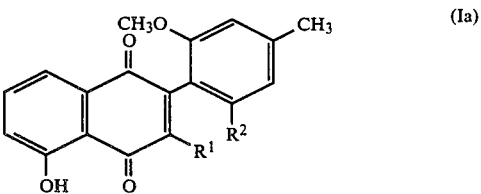

wherein $R^1$ and $R^2$ are hydrogen and carboxy, respectively; or $R^1$ and $R^2$ are hydroxy and carboxy, respectively; or $R^1$ and $R^2$ taken together represent

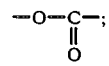

comprising cultivating a compound (Ia)-producing strain of the genus Streptomyces in a culture medium and harvesting the compound (Ia) from the resultant culture broth.

* * * * *